US006746455B2

(12) United States Patent
Beyar et al.

(10) Patent No.: US 6,746,455 B2
(45) Date of Patent: *Jun. 8, 2004

(54) BONE ANCHOR INSERTER WITH RETRACTABLE SHIELD

(75) Inventors: Mordechay Beyar, Caesarea (IL); Ze'ev Sohn, Modiin (IL)

(73) Assignee: AMS Research Corporation, Minnetonka, MN (US)

( * ) Notice: Subject to any disclaimer, the term of this patent is extended or adjusted under 35 U.S.C. 154(b) by 126 days.

This patent is subject to a terminal disclaimer.

(21) Appl. No.: 09/992,216

(22) Filed: Nov. 14, 2001

(65) Prior Publication Data

US 2002/0035369 A1 Mar. 21, 2002

Related U.S. Application Data

(62) Division of application No. 09/412,957, filed on Oct. 5, 1999, now Pat. No. 6,406,480, which is a continuation of application No. 08/733,798, filed on Oct. 18, 1996, now Pat. No. 5,972,000, which is a continuation-in-part of application No. 08/622,598, filed on Mar. 26, 1996, now Pat. No. 5,807,403, which is a continuation of application No. 08/150,517, filed on Nov. 10, 1993, now Pat. No. 5,520,700.

(60) Provisional application No. 60/012,205, filed on Feb. 23, 1996, and provisional application No. 60/005,348, filed on Oct. 18, 1995.

(30) Foreign Application Priority Data

Nov. 13, 1992 (IL) .................................................. 103737
Jan. 8, 1999 (IL) .................................................. 127978

(51) Int. Cl.[7] .............................................. A61F 17/88
(52) U.S. Cl. .................................................... 606/104
(58) Field of Search ............................ 606/73, 75, 86, 606/99, 164; 227/175.1; 81/436

(56) References Cited

U.S. PATENT DOCUMENTS

| 2,738,790 A | 3/1956 | Todt et al. |
| 2,979,089 A | * 4/1961 | Piesker |
| 3,995,619 A | 12/1976 | Glatzer |
| 4,172,458 A | 10/1979 | Pereyra |
| 4,569,469 A | * 2/1986 | Mongeon et al. |
| 5,013,292 A | 5/1991 | Lemay |
| 5,085,661 A | 2/1992 | Moss |
| 5,188,636 A | 2/1993 | Fedotov |
| 5,258,010 A | * 11/1993 | Green et al. |
| 5,281,237 A | 1/1994 | Gimpelson |
| 5,328,077 A | 7/1994 | Lou |

(List continued on next page.)

FOREIGN PATENT DOCUMENTS

| DE | 2 305 815 | 2/1973 |
| RU | 1225547 | 4/1986 |
| WO | WO 93/19678 | 10/1993 |
| WO | WO 98/19606 | 5/1998 |

OTHER PUBLICATIONS

Benderev, Theodore, Anchor Fixation and Other Modifications of Endoscopic Bladder Neck Suspension, Urology, vol. 40, No. 5, pp. 409–418, (Nov. 1992).

Blaivas J.G. et al., Pubovaginal Fascial Sling for the Treatment of Complicated Stress Urinary Incontinence, J. Urol. 145(6): 1214–1218 (Jun. 1991).

(List continued on next page.)

*Primary Examiner*—Ralph A. Lewis
(74) *Attorney, Agent, or Firm*—Jeffrey J. Hohenshell (57) ABSTRACT

A novel medical stapler and screw inserter device is disclosed herein wherein the medical instrument is formed in a non-linear or "C" or "V" shaped conformation. The nonlinear shape allows the physician to accomplish a per vaginal anchor or screw insertion into a patient's pubic bone, while locating the triggering hand outside of the vagina of the patient and employing a pulling force on the inserter/stapler, against the pubic bone of the patient. In addition, the weight of a patient's body may be used to counterweight the recoil effect to minimize stapler recoil during ejection of a staple from the stapler into a patient. Novel bone anchor screws and a related bone screw driver and a method of inserting it into the pubic bone through the vagina are also described for per vaginal bladder neck suspension procedures.

7 Claims, 8 Drawing Sheets

U.S. PATENT DOCUMENTS

| | | | |
|---|---|---|---|
| 5,413,598 | A | 5/1995 | Moreland |
| 5,439,467 | A | 8/1995 | Benderev et al. |
| 5,520,700 | A | 5/1996 | Beyar et al. |
| 5,544,664 | A | 8/1996 | Benderev et al. |
| 5,571,139 | A | 11/1996 | Jenkins, Jr. |
| 5,611,515 | A | 3/1997 | Benderev et al. |
| 5,633,286 | A | 5/1997 | Chen |
| 5,683,349 | A | 11/1997 | Makower et al. |
| 5,807,403 | A | 9/1998 | Beyar et al. |
| 5,836,314 | A | 11/1998 | Benderev et al. |
| 5,944,732 | A | 8/1999 | Raulerson et al. |
| 5,988,171 | A | 11/1999 | Sohn et al. |
| 6,039,686 | A | 3/2000 | Kovac |
| 6,053,935 | A | 4/2000 | Brenneman et al. |
| 6,322,492 | B1 | 11/2001 | Kovac |
| 6,328,686 | B1 | 12/2001 | Kovac |
| 6,328,744 | B1 | 12/2001 | Harari et al. |
| 6,334,446 | B1 | 1/2002 | Beyar |
| 6,387,041 | B1 | 5/2002 | Harari et al. |
| 6,544,273 | B1 | 4/2003 | Harari et al. |
| 2002/0107525 | A1 | 8/2002 | Harari et al. |

OTHER PUBLICATIONS

Precision Tack, Transvaginal Anchor System, The Precise Approach to Transvaginal Sling Procedure (advertisement), Boston Scientific Corporation, Microvasive, 4 pages (Jun. 1998).

Precision Twist, Transvaginal Anchor System, Low Profile Design for Precise Anchor Placement (advertisement), Boston Scientific Corporation, Microvasive, 4 pages (Jun. 1998).

Gittes, Ruben, et al., No–Incision Pubovaginal Suspension for Stress Incontinence, The Journal of Urology, vol. 138, pp. 568–570 (Sep. 1987).

Leach, Gary E., Bone Fixation Technique for Transvaginal Needle Suspension, Urology, vol. XXXI, No. 5, pp. 388–390, (May 1988).

Loughlin, Kevin, et al., Review of an 8–Year Experience with Modifications of Endoscopic Suspension of the Bladder Neck for Female Stress Incontinence, The Journal of Urology, vol. 143, pp. 44–45, (Jan. 1990).

Mascio, Valenzio C., et al., Therapy of Urinary Stress Incontinence in Women Using Mitek GII Anchors, Mitek brochure.

McGuire E. J., et al., Pubovaginal Sling Procedure for Stress Incontinence, J. Urol. 119(1): 82–84 (Jan. 1978).

McGuire E.J., The Sling Procedure for Urinary Stress Incontinence, Profiles in Urology, pp. 3–18.

McGuire E.J., Abdominal Procedure for Stress Incontinence, Urol. Clin. North Am., 12(2): 285–290 (May 1985).

McKiel, Charles F., et al., Marshall–Marchette Procedure Modification, The Journal of Urology, vol. 96, pp. 737–739, (Nov. 1966).

R.O. Parra, et al., Experience with a Simplified Technique for the Treatment of Female Stress Urinary Incontinence, British Journal of Urology, pp. 615–617.

Raz, Shlomo, Modified Bladder Suspension for Female Stress Incontinence, Urology, vol. XVII, No. 1, pp. 82–85, (Jan. 1981).

Spencer, Julia, et al., A Comparison of Endoscopic Suspension of the Vesical Neck with Suprapubic Vesicourethropexy for Treatment of Stress Urinary Incontinence, The Journal of Urology, vol. 137, pp. 411–415, Mar. 1987.

Stamey, Endoscopic Suspension of the Vesical Neck for Urinary Incontinence, Surgery, Gynecology & Obstetrics, vol. 136, pp. 547–554, (Apr. 1973).

Webster, George D., Female Urinary Incontinence: Stress Urinary Incontinence, 6 pages (1987).

Winter, Chester C., Peripubic Urethropexy for Urinary Stress Incontinence in Women, Urology, vol. XX, No. 4, pp. 408–411(Oct. 1982).

* cited by examiner

BONE ANCHOR INSERTER WITH RETRACTABLE SHIELD

RELATED APPLICATIONS

The present application is a divisional application of U.S. patent application Ser. No. 09/412,957 filed on Oct. 5, 1999 now U.S. Pat. No. 6,406,480, which is a continuation of U.S. application Ser. No. 08/733,798, filed Oct. 18, 1996, now U.S. Pat. No. 5,972,000; which is a continuation-in-part of U.S. application Ser. No. 08/622,598, filed Mar. 26, 1996, now U.S. Pat. No. 5,807,403; which is a continuation of U.S. application Ser. No. 08/150,517, filed Nov. 10, 1993, now U.S. Pat. No. 5,520,700; which claims priority to Israeli Patent Application No. 103,737, filed Nov. 13, 1992. The present application also claims priority to Israeli Patent Application No. 127,978, filed Jan. 8, 1999; U.S. patent application Ser. No. 09/287,867, filed Apr. 7, 1999 (pending); U.S. Provisional Application Serial No. 60/012,205, filed Feb. 23, 1996; and U.S. Provisional Application Serial No. 60/005,348, filed Oct. 18, 1995. The present application claims the domestic and foreign priority benefits of all these prior applications. These prior applications are herein incorporated by reference.

FIELD OF THE INVENTION

The present invention relates to a bone anchor, bone anchor screw, and an inserting device for use in medical applications, and particularly in medical suturing. The invention is especially useful in treating female urinary stress incontinence, although it can be utilized with other medical applications as well.

BACKGROUND OF THE INVENTION AND DESCRIPTION OF THE PRIOR ART

Urinary stress incontinence, i.e., the inability to control urination from the bladder, is a distressing problem for more than ten percent of elderly women as well as for many young women. This condition frequently arises in the following manner: in a normally anatomically positioned bladder, the proximal urethra and the bladder are in pressure continuity with the abdominal cavity, so that an increase in abdominal pressure is transmitted both to the bladder and to the proximal urethra, resulting in normal continence. However, particularly among elderly women, the bladder and the proximal urethra tend to descend from their normal anatomic positions such that the bladder neck and proximal urethra move away from the posterior wall of the pubic bone. When this occurs, the proximal urethra is no longer in pressure continuity with the abdominal cavity; therefore, an increase in intra-abdominal pressure (e.g. by laughing or coughing) results in an increase in intravesical pressure, but no change in the urethral closing pressure, thereby producing so-called stress incontinence. It also appears that as the bladder descends, the urethra becomes shorter and curved, so that its radial tonic muscle contraction is reduced, contributing to incontinence. Another pathology may arise from urethral sphincteric damage.

The surgical treatment for stress incontinence involves bladder neck suspension. One treatment is by an open surgical operation, involving an incision in the abdominal wall and/or anterior vaginal wall, to reposition and suspend the bladder and proximal urethra to their normal anatomic positions. This is done by suspension of the bladder neck and periurethral tissue to the posterior wall of the pubic bone. In another surgical procedure, the bladder neck is elevated by suspension of suture threads passing, with the aid of long needles, from both sides of the urethra and the bladder neck to the lower abdominal fascia or superior pubic bone ramus.

In prior patent application Ser. No. 08/150,517 filed Nov. 10, 1993 and its continuing application (the disclosures of both of which are hereby incorporated by reference) the inventors have disclosed apparatus and method(s) which allows treatment of stress incontinence by incisionless per vaginal bladder neck suspension. As disclosed therein, an inserter device can be utilized for ejecting and implanting a staple or bone anchor through the vaginal tissue to enter the pubic bone. In another embodiment, as further discussed hereafter, an inserter device can be used to install a bone anchor by screwing the bone screw into the pubic bone, with or without vaginal incision. The suture thread that is secured to the bone anchor, staple or bone screw, suspends the bladder neck and the periuretiral tissue to the posterior wall of the pubic bone.

It has been found, however, in stapler devices, and especially those that require high impact for bone implantation, that the ejection of the staple from the device causes the stapler to recoil. As is apparent from basic physics, the action of ejecting the staple from the stapler is associated with a reaction force which forces the inserter/stapler, and the hand of the individual (the physician) implanting the same, to move backwards. As a result, the physician must take this recoil into account and use force to firmly press the stapler against the pubic bone to ensure that the bone anchor is properly and effectively ejected and implanted. Anyone familiar with carpentry-type staple guns is familiar with this recoil. If pressure is not placed over the head end of the stapler, and the surface into which the staple is driven is hard (as in the case of bone), the staple will not be fully implanted, but, rather, the user's hand will recoil. The medical stapler should also be held perpendicular to the bone surface. The stapler must be held in that position with the stapler held firmly during and through the ejection process so that the stapler does not shift its position as a result of the recoil. Otherwise, undue movement of the stapler because of recoil can result in a staple being ejected in an incorrect orientation, or incompletely ejected into the bone of the patient. This problem is especially apparent where the material into which the staple is ejected is bone and the physical confines of the space where the medical physician's hands are working is limited, i.e., within a vagina.

Similarly, where the inserter is a screwdriver type and the anchor is a screw type anchor, unless a hole is pre-drilled in the insertion site, constant firm pressure must be applied through the axis of the anchor (perpendicular to the pubic bone) to assist the self tapping property of the anchor to facilitate insertion during screwing. The medical screwdriver type inserter must, therefore, be held in the correct position relative to the patient's anatomy through the insertion process.

A purpose of the present invention is to provide leverage, which facilitates a constant pressure at the insertion site to minimize the effect of this recoil, increasing the ease of use of an inserter device in a medical procedure (whether a pusher or impact type inserter, or a screw inserter), and increasing an inserter device's effectiveness. This furthers the self-tapping property of the bone anchor, whether it be an impact type or screw type anchor. A screw type inserter device increases the ease of use of an inserter device in a medical procedure and increases the present stapler device's effectiveness.

A further purpose of the present invention is to provided leverage in the per vaginal insertion of a bone anchor into the pubic bone. The present invention allows the physician to employ a pulling force perpendicularly against the pubic bone of the patient, and to conveniently do so with one hand. The leverage, degree of accuracy and ease of insertion are believed to be significantly enhanced by the present invention.

In one embodiment, the invention relates to per vaginal bone screw insertion without drilling a hole in the bone by use of a non-linear or C-shaped inserter having a rotating intravaginal head for per vaginal bone screwing with or without vaginal wall incision. An additional purpose of the present invention is to provide a screw type bone anchor and related device and procedure for per vaginal incisionless or minimal incision bladder neck suspension.

SUMMARY OF THE INVENTION

The present invention addresses the difficulties experienced in the prior art by providing a "C", "V" or other non-linear insertion shaped device for use in medical applications, and especially, per vaginal insertions of anchors of any type into the pubic bone of a patient. The insertion device, which may be rigid or flexible, is positioned during use so that force may be applied through the axis of the anchor. The weight of a patient can contribute to the force applied by the physician to firmly press the device against the patient's anatomy, so as to minimize the effects of the problems normally associated with recoil. Although the present device is directed toward a stapler device for use to eject a staple type bone anchor, it will be appreciated that the pusher/driver portion of the device can alternatively be used to insert a screw type bone anchor and will be useful in other applications as well.

Accordingly, it is an object of the present invention to provide an insertion device which minimizes recoil during ejection of a bone anchor into bone.

It is further an object of the present invention to provide an insertion device which minimizes recoil during per vaginal insertion of a bone anchor into the pubic bone and otherwise allows constant pressure to be applied during the per vaginal insertion of self-tapping anchors into the pubic bone.

It is a further object of the present invention to provide a device which facilitates additional pressure to be applied to the insertion site beyond the direct pushing pressure applied by the physician in the case of a linear inserter held in place in the vagina by the physician's hand. With the present inserter, the physician's hand is used to pull the inserter against the resistive force of the pubic bone, thereby forcing the anchor tip to penetrate the bone cortex. It is far easier to insert a bone anchor, staple or screw with the hands external to the vagina and by use of the pulling force perpendicular to the bone surface.

It is further an object of the present invention to provide an inserter device for medical applications which improves the accuracy and effectiveness of anchor insertions.

It is further an object of the present invention to utilize the physical pulling force on the inserter to further fixate the anchor tip penetration force perpendicular to the bone surface and in line with the physician pulling force.

It is further an object of the present invention to utilize at least a portion of the weight of a patient's body to maintain a bone anchor or screw inserter in firm contact with the patient during insertion of a bone anchor or screw into the patient's bone.

It is a further object of the present invention to use at least a portion of the weight of a patient as counter balancing leverage against the recoil of a bone anchor/staple/screw being inserted into the bone of a patient.

It is further an object of the present invention to provide an improved inserter device for inserting bone anchors, staples and/or screws in medical procedures.

It is further an object of the present invention to provide an improved bone anchor inserter for use in and to facilitate medical applications.

It is further an object of the present invention to provide improved bone anchors and bone anchor inserters.

It is further an object of the present invention to provide improved bone anchors and bone anchor inserters for treatment of female urinary stress incontinence and medical applications.

It is further an object of the present invention to provide an improved method for treatment of urinary stress incontinence.

It is further an object of the present invention to provide an improved method for treatment of urinary stress incontinence including per vaginal bone anchor insertion into the pubic bone. These bone anchors are either in the form of staples or screws. The bone anchor has either a non-linear (e.g. a "C" or "V" shape) or linear shape and is operated either by an impact or by a rotational movement to insert or screw a bone anchor, staple or bone screw into the bone with or without vaginal wall incision.

BRIEF DESCRIPTION OF THE DRAWINGS

FIG. 1b is a bottom, back, and left side perspective view (on a different scale) of the stapler or pusher/impact type bone anchor inserter of FIG. 1a.

FIGS. 1d(1)–1d(6) are front views of bone screws for use in the screwdriver-type bone anchor inserter of FIG. 1c. Several different bone screw embodiments are shown, in accordance with the present invention.

DETAILED DESCRIPTION OF THE DRAWINGS AND THE PREFERRED EMBODIMENTS

The present invention relates to an improved inserter device (whether a stapler or screw inserter) for inserting a bone anchor (whether staple or screw) into a patient. The inserter is shaped in a "C" shaped design which allows the physician's pulling force to press the staple or screw into the bone before and during ejection or screwing of a bone anchor. As a consequence, the physician is able to use a pulling, force against the resistive force of the pubic bone rather than a pushing, force against the recoil of the inserter. The device also allows the physician to use the weight of a patient's body as counterbalancing leverage to minimize recoil of the staple during ejection of a staple into the patient's body. In addition, the novel geometry of the inserter allows the physician to hold the inserter and perform a per vaginal procedure with one hand out of the vagina.

Figure 1A:
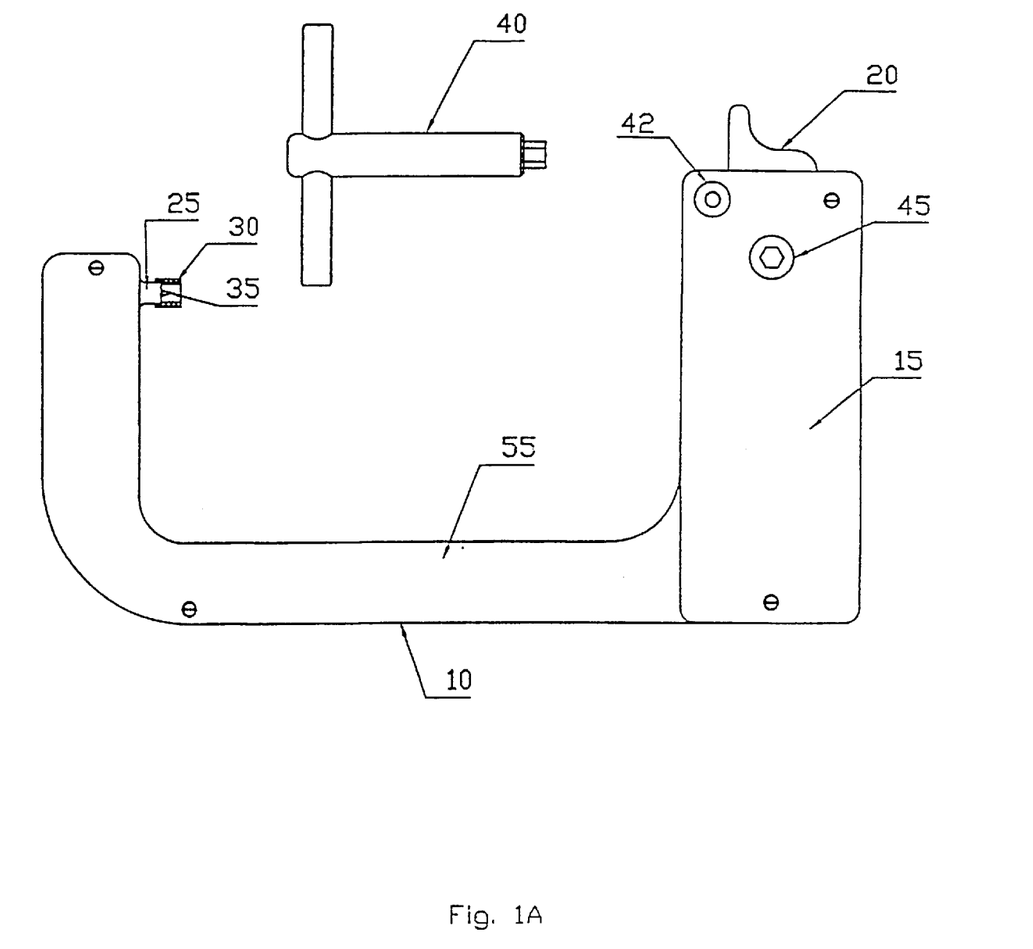
FIG. 1a is a left side view of a stapler or pusher/impact type bone anchor inserter, in accordance with the present invention, with a front view of a loading key shown as well.
Figure 1B:
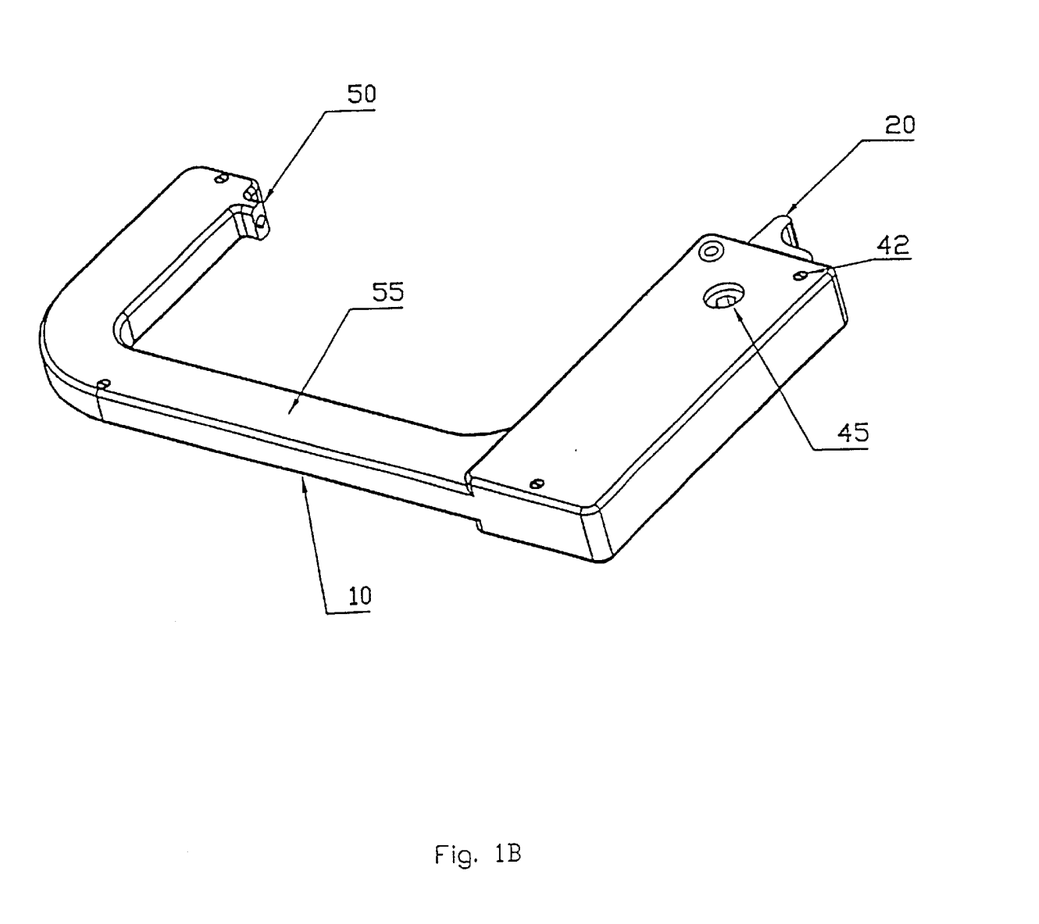

As shown in FIGS. 1a and 1b, a stapler or bone anchor inserter 10 is disclosed having a handle 15, trigger 20, anchor housing 25 and an anchor shield 30. Handle 15 is attached to body 55 of the bone anchor inserter 10. Body 55 is curved such that when attached to the handle 15 the two components form a "C" shaped apparatus. The inserter can be formed as a V-shape or another non-linear configuration.

In use, a drive pin (not shown, but located within the body) forces the anchor 35 (See FIG. 6, without suture thread shown, for ease of illustration) out of anchor housing 25, which is part of barrel 50 (see FIG. 1B) of the stapler 10. The stapler or bone anchor inserter 10 may be made of any suitable material, for example, stainless steel which meets surgical instrument standards. An internal spring mechanism (not shown) is in mechanical contact with the ejector pin (which is placed in contact with the bone anchor or staple). Upon the activation of the trigger 20, the ejector pin comes into contact with the bone anchor or staple 35, providing the forcible ejecting, pushing and implanting of the bone anchor or staple 35, with attached suture thread, into bone. The ejection mechanism is activated by the trigger 20 which can be provided with a safety release or lock-out 42 to prevent accidental, premature staple discharge.

Figures 6, 7, 8:
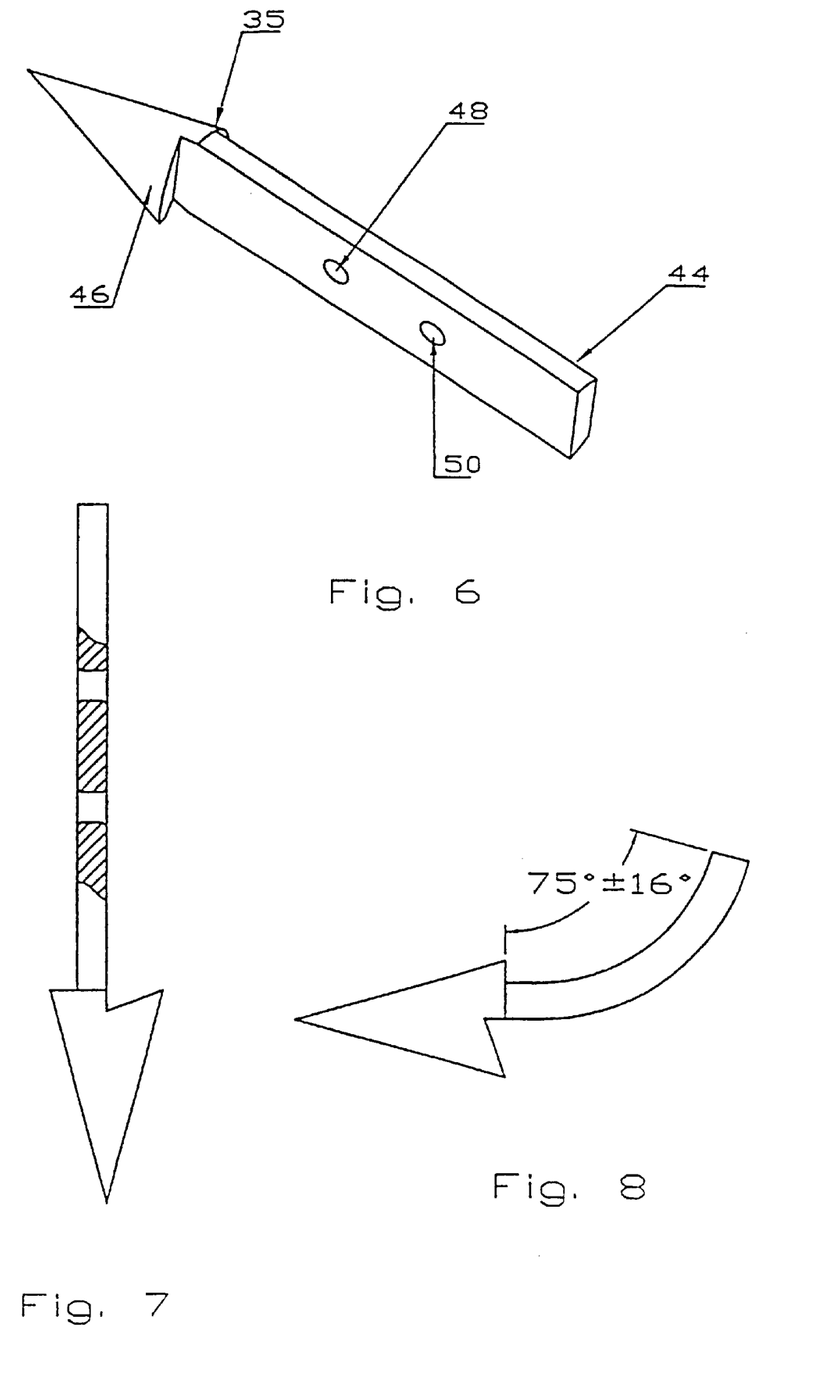
FIG. 6 is a bottom, front and left side perspective view of one form of a bone anchor used with the stapler/bone anchor inserter described herein.
FIG. 7 is a front view of the stapler type bone anchor shown in FIG. 6 which can be used with the staple inserter. In this figure, one example of a bone anchor with an offset tip is shown, i.e. a bone anchor in which the central, longitudinal axis of the tip is offset from the central, longitudinal axis of the bone anchor's shaft or body. An offset tip can be provided to a staple type bone anchor or to a screw type bone anchor.
FIG. 8 is a front view of the curved shape that a bone anchor (e.g. that shown in FIG. 6 or 7) can achieves after insertion into bone, a consequence of it having been formed of shape memory alloy and the temperature of the staple having changed to its state changing temperature.

The tail end of the anchor 35 (best seen in FIGS. 6–8) is held in a nearly straight configuration within anchor housing 25 until ejection. The anchor housing 25 is attached to the inserter 10 prior to use, remains attached to the inserter during anchor insertion and, after insertion of the bone anchor, is disposable. A retractable anchor shield 30 surrounds and protects the sharp conical front end of the anchor, to ease insertion. The bone anchor 35 (the specific anchor 44 is shown in FIGS. 6–8) is implanted into the bone without pre-drilling of a hole in the patient's bone. After cocking the internal spring mechanism using a loading key 40, which is placed into and rotated within loading socket 45, and attaching a bone anchor housing 25 (with a sutured anchor 35 or 44), the bone anchor inserter 10 is ready for use. The spring mechanism stores the mechanical energy necessary to eject and insert the anchor into bone. In one preferred embodiment, this is approximately 2.95 Joule ±10%.

Figure 1C:
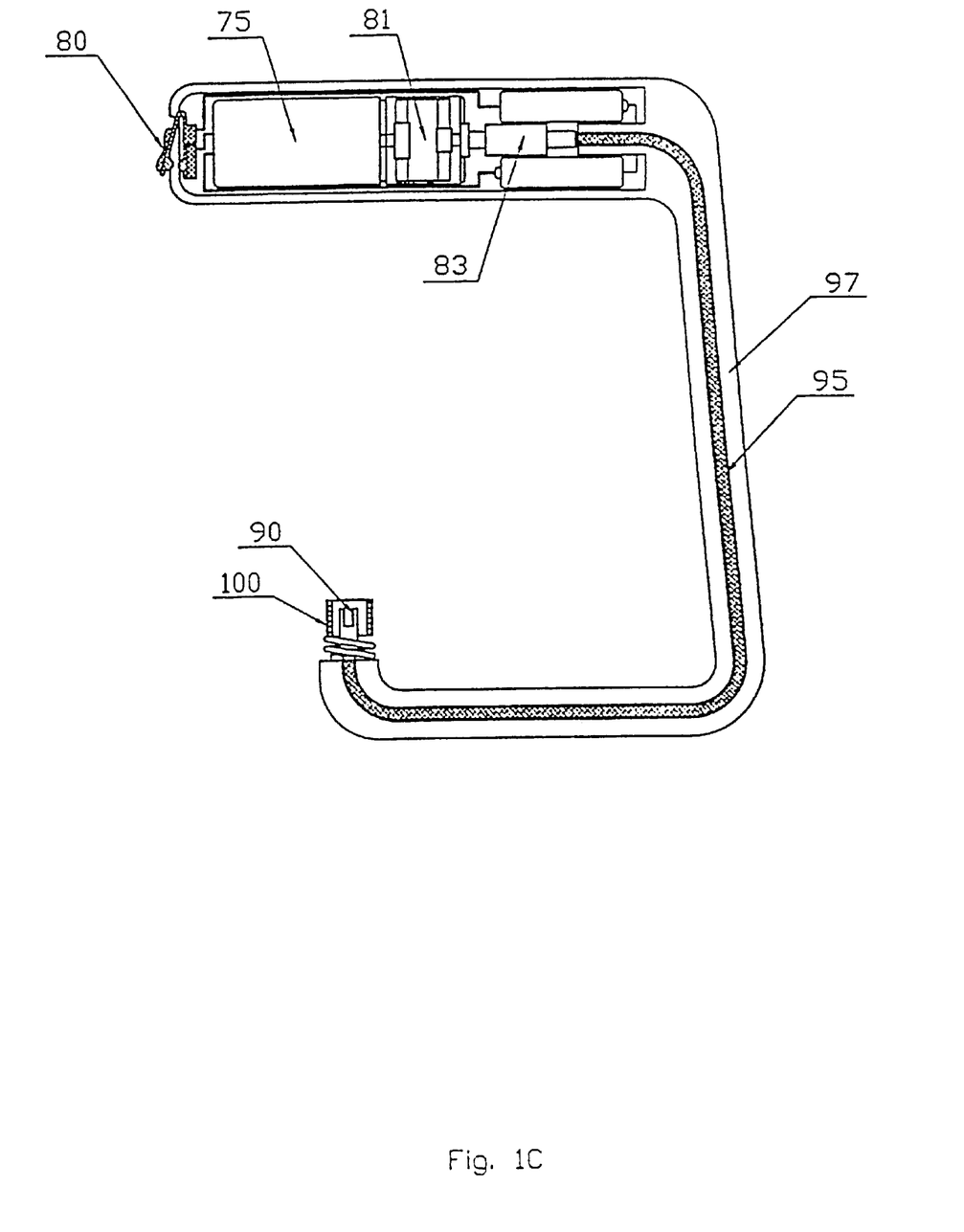
FIG. 1c is a right cross-sectional view of a screwdriver-type bone anchor inserter for rotational insertion of bone screws.
Figure 1D:
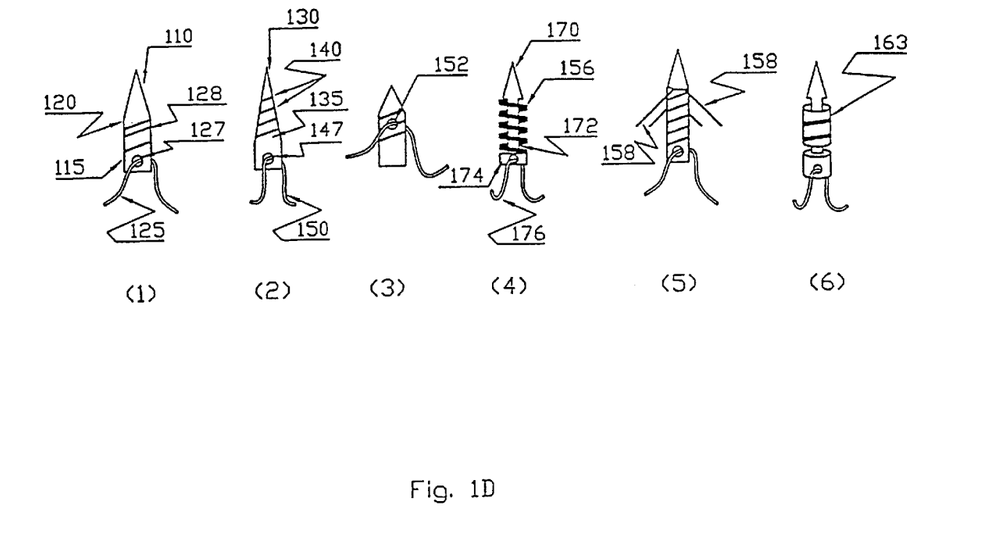

FIG. 1c illustrates a C-shaped bone anchor driver in a shape allowing rotational insertion of a bone screw into a bone through a body orifice such as the vagina. The inserter consists of a handle 70 having a battery-operated rotating motor 75 with a switch 80 to control operation. The motor's rotational movements are linked to a gear box (gear 81 and gear to shaft adapter 83) to allow more torque. The rotation is transferred from the gear box through the inserter device to the screw adapter 90, via a flexible shaft 95, a flexible shaft guide 97 may be provided, as well, if desired.

The anchor is connected to screw adapter 90, which is at the second end of the inserter, the end opposite the handle. The anchor or screw is disconnected once the screw is implanted into the bone surface. The screw protector or retractable shield 100 shields the sharp tip of the screw until it is well positioned, so as not to accidentally damage the patient's tissue. Once the inserter is well positioned, pulling the handle 70 retracts the spring-biased screw protector or retractable shield 100 thereby allowing the screw's sharp tip to penetrate the soft tissue. In another embodiment, the screw protector or retractable shield 100 may have a rough edge surface, or small pins or sharp tips to hold the soft tissue (such as vaginal mucosa) and to prevent surrounding tissue rotation as the anchor screw rotates and penetrates the soft tissue and into the bone. Clearly, then, depressing switch 80 activates the motor 75 which drives the flexible shaft 95 connected to the screw adaptor 90. This causes a screw (see FIGS. 1D) to become embedded into the bone.

Figure 1E:
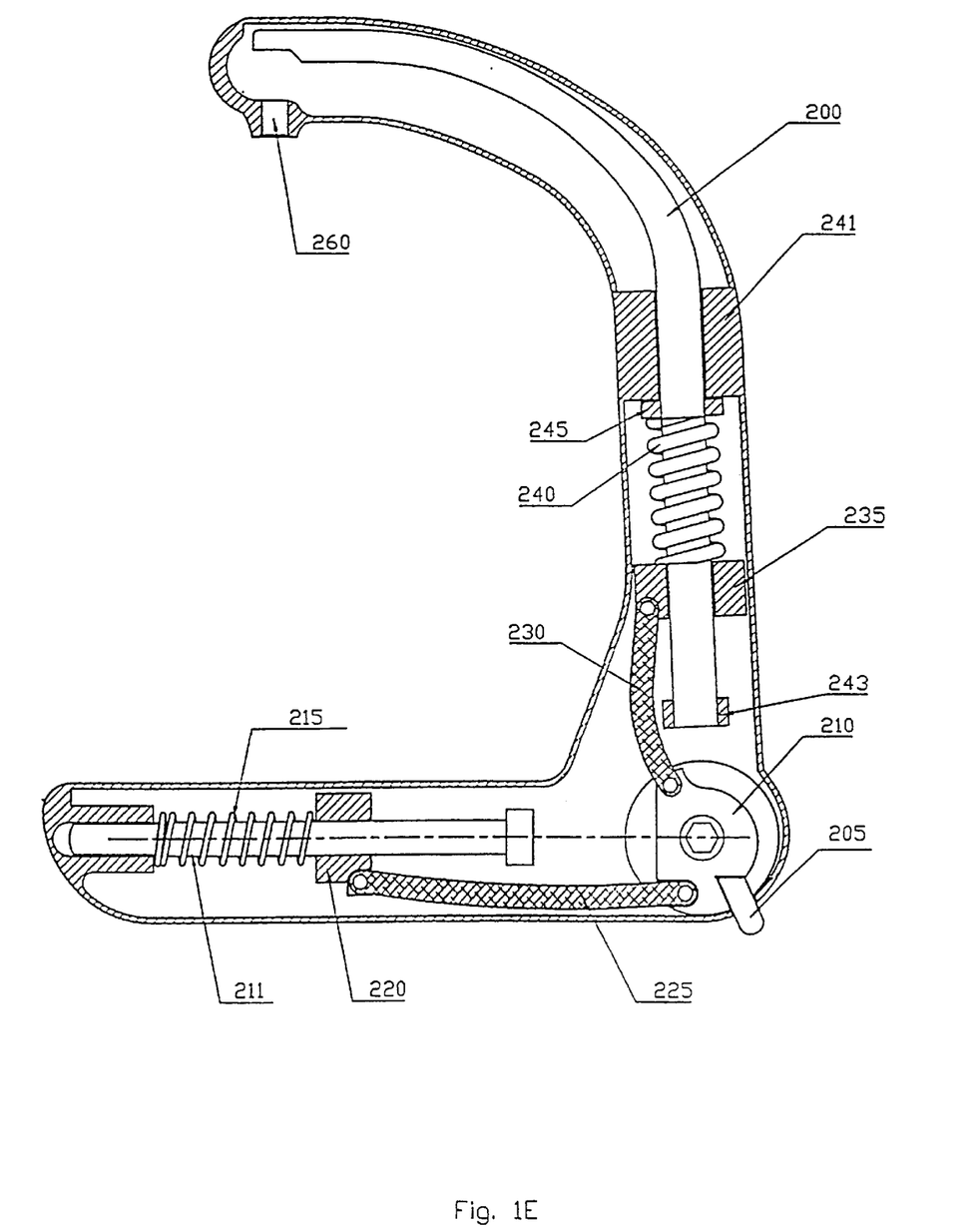
FIG. 1e is a right cross-sectional view of a spring loaded C-shaped inserter, having an alternative spring mechanism.

FIG. 1e shows an alternative, spring-loaded C-shaped inserter, having a different spring mechanism to that shown in FIGS. 1a & 1b. The inserter has a two spring mechanism which allows the user to impart more energy and impact to the anchor during implantation into the bone. At the same time, this inserter has the significant advantage that the two spring design results in cancellation of the rotational movement that the inserter may have during release. This results in a more stable anchor insertion.

This alternative inserter embodiment utilizes a hammer 200 which impacts and ejects an anchor into a bone. When safety 205 is not in place blocking the movement of connecting rod 210, second spring 215 can expand outward from its compressed state against second weight 220 to force second rod 225 forward to rotate connecting rod 210. Connecting rod 210 is connected to both second rod 225 and to main rod 230. Rotation of the connecting rod 210 in the counterclockwise position by second rod 225, as shown in FIG. 1e, moves main rod 230 away from its position up against main weight 235 which causes hammer 200 to impact a bone anchor.

More specifically, while main rod 230 is forced against main weight 235, the hammer 200 is maintained in a stationary position and primed for subsequent movement to eject a bone anchor held in recess 260. Main spring 240 is connected to main weight 235, with main weight 235 connected to hammer 200. A friction disk 245 is provided above main spring 240. A hammer guide 250 is provided around a portion of the hammer 200, as shown in FIG. 1e. Before activation of the inserter, main spring 240 is maintained in a compressed position. Movement of main rod 230 away from main weight 235 allows main spring 240 to expand outward, forcing main weight 235 and hammer 200 downward. The release of the energy stored in main spring 240 thus forces hammer 200 downward to impact and eject a bone anchor out of recess 260 and into a bone.

Figure 2:
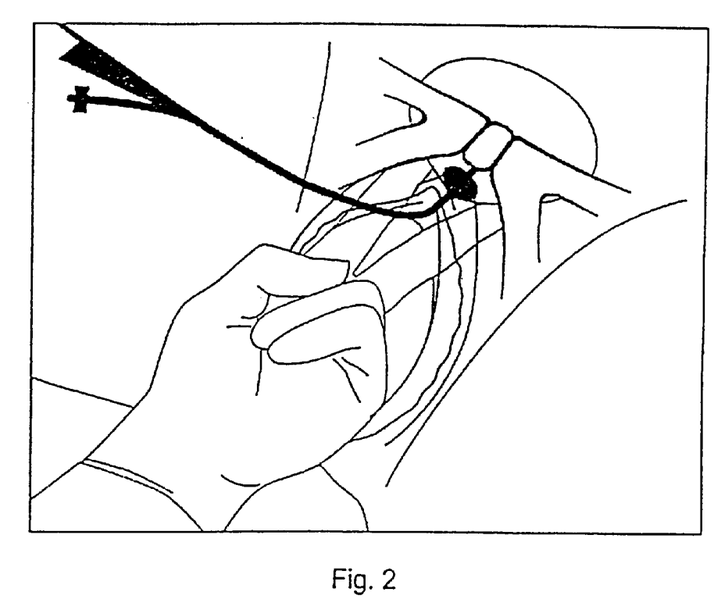
FIG. 2 is a perspective view of a catheter inserted into the bladder of a patient in accordance with the method of the present invention, with a physician's (or health care worker's) two fingers partially inserted into a woman's vagina.

The method of the present invention is shown in FIGS. 2–5. With the patient in lithotomy position, the surgical area and the vagina are cleaned and disinfected. A Foley catheter is inserted inside the bladder, and the balloon is inflated with approximately 10–20 cc of water. The catheter is then pulled backwardly to locate the balloon just above the bladder neck as shown in FIG. 2.

Figure 3:
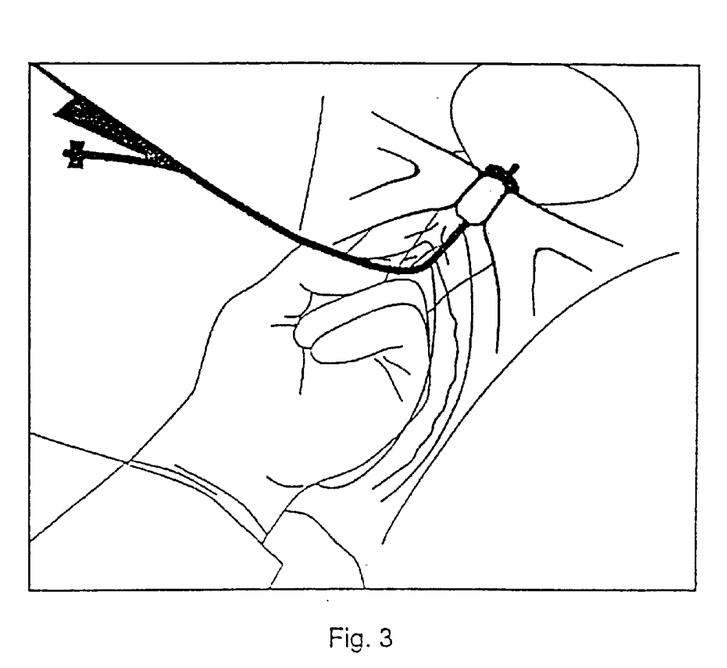
FIG. 3 is a perspective view of the hand of the physician pressing the anterior vaginal wall of a patient against the posterior of her pubic bone, according to the present method (again with the catheter in place).

The catheter (within the urethra) and the balloon at the bladder neck are palpated by the physician's finger tips. Pressing the fingers upward and forward, the anterior vaginal wall is pressed against the posterior pubic bone surface, as shown in FIG. 3.

The bone anchor inserter (whether a stapler/impact or a screwdriver-type inserter) is then inserted into the vagina (see FIG. 4) near the bladder neck and approximately 2 cm. to the side of the urethra. The inserter is pulled against the pubic bone. Notice that the triggering hand of the physician is external to the vagina and that the force applied by the physician is one of pulling against the resistive force of the pubic bone. The tip of the bone anchor 35 touches and penetrates the vaginal wall and enters the cortex of the pubic bone.

Figure 4:
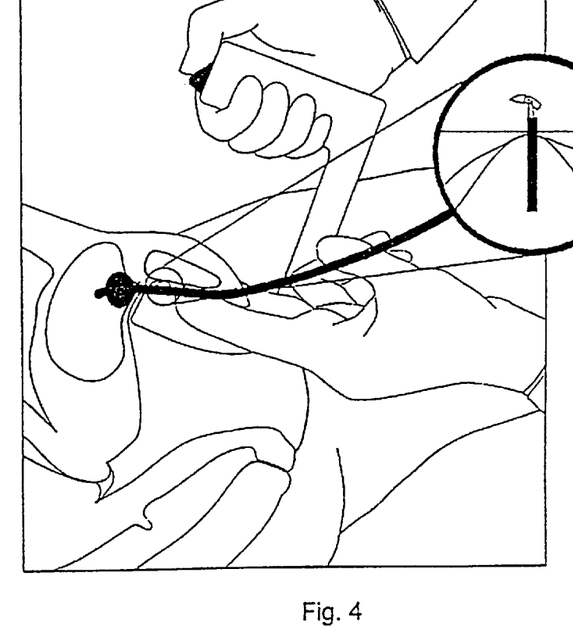
FIG. 4 is a perspective view of the bone anchor non linear inserter (in this case, a C-shaped inserter) inserted into the vaginal canal, with the anchor housing pressing the anterior vaginal wall of the patient against her pubic bone. Notice that the physician's hand, which is used for triggering the mechanism of the inserter, is outside of the vagina and that the physician can pull the inserter against the resistive force of the pubic bone. An enlarged inset cross-sectional view is provided of the insertion step of the bone anchor into the pubic bone.

Thus, once the inserter is stable and properly positioned in the vagina, the trigger 20 (or switch 80, for the screw inserter of FIG. 10) is pulled and the bone anchor 25 penetrates and fixates within the bone. When the end of the inserter 10 is under the pubic bone, and pressed against it, the physician pulls up on the handle 15 of the stapler or bone anchor inserter 10. By doing so, the physician lifts the anchor 35 or screw 120 and anchor housing 25 or screw adaptor 90 against the pubic bone. A portion of the weight of the patient resists the lifting of the inserter, pressing against it firmly. As a result, the lifting of the stapler or bone anchor inserter 10 is performed against some of the weight of the patient, ensuring a firm and effective contact of the anchor tip with the pubic bone. Mechanically, it is easier for the physician to pull on the inserter with his or her hand outside of the vagina than for the physician to have his or her triggering hand within the vagina and pushing the inserter against the pubic bone. The penetration of the tip of the bone anchor into the bone cortex before ejection or screwing further increases the stability of the ejection into the pubic bone. The use of the C-shaped inserter allows at least part of the patient's weight to counterbalance the recoil of the spring mechanism. The patient's body weight, along with the inserter's shape, provides the physician with suitable leverage for ensuring penetration of the anchor 35 or screw 120 into the pubic bone. This is especially important in the use of the present bone anchor device which, in the case of the ejected anchor, seeks to avoid predrilling of a hole, followed by anchor insertion.

Releasing the safety 42 first and then pressing the trigger 20 of the device activates the inserter spring mechanism (not shown) which ejects the anchor 35 to a prescribed depth within the bone (e.g. 2.5 mm) so that no portion of the anchor protrudes from the bone surface. Although the end of the inserter will experience a reaction force when the staple is ejected, the weight of the patient, pressing downward against the inserter end (anchor housing 25 and anchor shield 30) combined with the force exerted by the physician by pulling the handle 15 of the bone anchor inserter 10 upward (so that the end of the inserter is forced against the weight of the patient and the penetration of the tip of the anchor into the pubic bone before ejection) result in a firm and solid contact between the inserter and the pubic bone during and through the insertion process, minimizing any problems of insertion associated with stapler recoil.

Two to four anchors are preferably inserted into the patient. Bone anchors are inserted on each side of the urethral axis or parallel along each side of the posterior aspect of the superior pubic bone ramus, lateral to the symphysis pubis. When four bone anchors are used, two bone anchors are inserted on each side of the urethral axis or parallel along each side of the posterior aspect of the superior pubic ramus, about 2 cm. lateral to the symphysis pubis. Each pair of two bone anchors is inserted with the two bone anchors in a pair approximately 2 cm. apart. Cystoscopy is then performed to verify that there are no bladder or urethral perforations.

Figure 5:
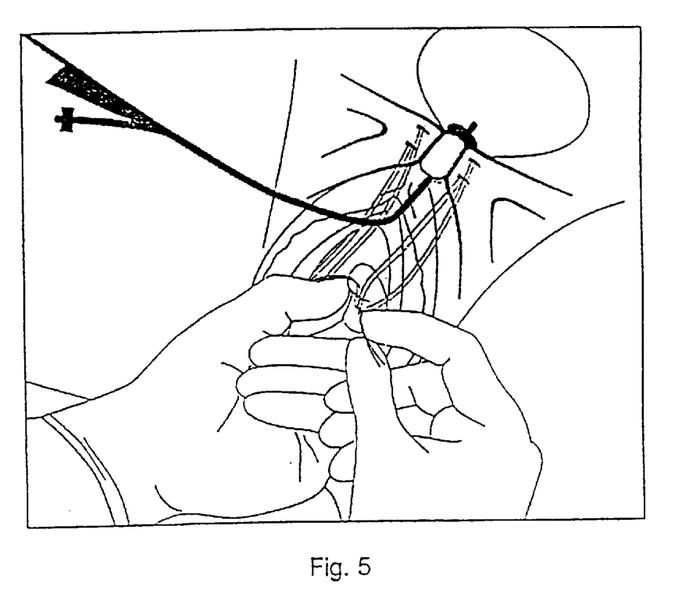
FIG. 5 is a perspective view of the hands of the physician tying the suture threads affixed to the bone anchors (the bone anchors having first been ejected or screwed, and implanted into the patient's pubic bone).

The suture threads extending from the anchors are then tied. For example, when inserting four bone anchors, four sets of suture threads should protrude from the vaginal wall. The suture threads are tied from one bone anchor to the other, ipsilaterally on each side of the urethra, as shown in FIG. 5. They may be tied either above the vaginal mucosa or below the vaginal mucosa (using a deshamp) with or without vaginal dissection. The tie may be left as is or pushed beneath the mucosa.

Suprapubic or Foley urethral catheterization is then performed. The suprapubic catheter is to remain until complete bladder emptying is achieved by normal urination. Prophylactic antibiotic is administered perioperatively. Physical strain and lifting by the patient is to be avoided for approximately 2–3 months.

In one recornmended embodiment, the bone anchor can be made of a single piece of a shape memory alloy, such as the nickel-titanium alloy called Nitinol. One form of bone anchor, for example, which can be used with the present invention, has a conical front end 46 (See FIGS. 6–8) with diameters ranging from 1.9–2.4 mm, and a tail end with a nearly rectangular cross-section. The tail portion is preferably 6.0 mm long with a width that ranges from 1.9–2.4 mm and a thickness of about 0.6 mm. The anchor tail 44 contains two holes 48 and 50 which are used for threading the suture. An example of a suture thread which can be used in the bone anchor is sterile polypropelene monofilament No. 1. The bone anchor is depicted in FIGS. 6 through 8. According to the preferred embodiment of the bone anchor 35, the longitudinal axis of the tail end is offset from the center axis of the conical tip 46. This is best seen in FIGS. 7 and 8.

Within the bone medulla, the bone anchor 35 soon heats to body temperature, changing by shape memory alloy, for example, from a straight to a curved shape, i.e., the longitudinal axis of the anchor changes, after insertion. This is shown in FIG. 8. According to one preferred embodiment, the end of the tail and the rear end of the conical tip, after heating of the bone anchor sufficient to change its shape, will subtend an angle of about 75°±16° (as seen in FIG. 8). This change of shape is because of the fabrication of the anchor from shape memory alloy. This curved shape fixes the anchor within the bone and inhibits the inadvertent removal of the anchor. Pulling on the suture, which is connected to the anchor 35, causes the anchor to rotate and further fixate in the bone. The reformation of the anchor to its curved shape (the shape it had prior to straightening by being held in the anchor housing 35) and rotation, together, prevent the anchor from exiting through the entrance path provided into the bone. The small profile and sharpness of the anchor tip 46 allow easy insertion inside the bone with minimal damage to the bone surface.

Thus, the present invention provides an apparatus and method which (in the anchor ejection mode) does not require pre-drilling of the bone or soft tissue dissection to insert the bone anchor into the bone. Similarly, the bone anchor does not require cement or other fixative to remain in place.

The bone anchor and bone anchor inserter are supplied sterile. As the bone anchor inserter is a multiple use device, the inserter (and its loading key) should, of course, be cleaned and sterilized before each new patient procedure. Cleaning is accomplished by washing and rinsing the inserter and loading key with water and a liquid detergent, while scrubbing with a flexible brush to completely remove all traces of blood. The inserter and loading key should be rinsed thoroughly with water to remove detergent residues. Panels in the inserter body allow access for cleaning. Once cleaned, the inserter and loading key may be cloth or air dried. The inserter and loading key may be sterilized by heat or steam autoclave, or gas (EtO), in accordance with hospital procedures for sterilization of stainless steel surgical instruments.

Various different types of bone screws 120 can be used in accordance with the present invention. As shown in FIG. 1d(1), a bone screw is disclosed having a conical tip 110 and a screw body 115. The diameter of each of the screw threads 128 (the grooves, recesses or indentations in the material of the screw) is constant along the screw body. The suture 125 is attached at a hole in the end 127 of the bone screw.

FIG. 1d(2) shows a bone screw 120 with a more tapered conical tip 130 and a screw body 135. In this version, the diameter of the screw threads 140 vary. The diameters of the screw threads 140 increase from small diameters near the apex of the conical tip to greater diameters near the screw body 135. The screw threads 140 can be located on all or a portion of the screw body as well, if desired. The suture 150 is attached through a hole in the end 147 of the screw.

FIG. 1d(3) is similar to FIG. 1d(1). In this figure, however, the suture is shown attached through a hole in the middle 152 of the bone screw.

FIG. 1d(4) shows a bone screw 120 in which the screw threads or grooves are formed by wrapping spring wire 156 around a solid body. The body has a leading tip 170 and a shaft 172, of smaller relative cross section. A trailing end 174 with a hole is provided for attaching the suture thread 176. The spring wire is wrapped on the shaft 172 and maintained between leading tip 170 and the trailing end 174.

FIG. 1d(5) shows a bone screw similar to that in FIG. 1d(4). In this screw, leaf springs 158 are provided. Leaf springs 158 are initially flattened against the side surface of the bone screw, i.e., when the screw is inserted into the bone. Upon insertion, however, the leaf springs 158 expand outward from a compressed to a noncompressed state (due to the elasticity which is characteristic of a spring) to provide greater anchoring of the bone screw within the bone.

FIG. 1d(6) discloses a bone screw in which the screw threads or grooves are formed by wrapping a spring plate 163 around the screw body or shaft of the screw. Here, too, the spring plate is held between the leading tip and the trailing end.

The bone screw is typically made of a medical grade alloy such as Stainless Steel 316. Its sharp tip and small diameter allows for its penetration through the vaginal wall and the periosteum, without pre-drilling a hole. As the screw is rotated by the inserter, which may be linear or C-shaped, it further enters the bone until it reaches a prescribed depth within the bone. The screw then automatically disconnects from the rotating inserter shaft. The medical technique of inserting a bone screw into the pubic bone through the vagina for the purposes of bladder neck suspension is also within the scope of the present invention, as is the bone screw inserter.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the appended claims.

We claim:

1. A method of placing a bone anchor in a patient during an incontinence procedure, the method comprising:

identifying a target bone anchor site on a posterior portion of a pubic bone of a patient;

moving said bone anchor to a location proximate said bone anchor site;

inserting said bone anchor into said bone anchor site with a motive force; and providing energy for said motive force from a source outside of energy provided by a human user at the time said bone anchor is being inserted/to said bone anchor site.

2. A method as set forth in claim 1, wherein the energy is provided from stored energy source.

3. A method as set forth in claim wherein the energy is provided from battery energy.

4. A method as set forth in claim 1, wherein the energy is provided from pneumatic energy.

5. A method as set forth in claim 1, wherein the energy is provided from spring energy.

6. A method as set forth in claim 1 wherein the energy is provided from electrical energy.

7. A method as set forth in claim wherein the step of moving said bone anchor to a location proximate said bone anchor site includes the step of making at least one vaginal incision and placing a device that includes the bone anchor through said vaginal incision.

* * * * *